United States Patent [19]
Kooy et al.

[11] Patent Number: 5,961,454
[45] Date of Patent: *Oct. 5, 1999

[54] FUSION OF ANATOMICAL DATA SETS INTO STEREOTACTIC COORDINATES

[75] Inventors: Hanne M. Kooy, Newton, Mass.; Marcell Herk, Amsterdam, Netherlands

[73] Assignee: The Brigham and Women's Hospital, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/755,731

[22] Filed: Nov. 25, 1996

Related U.S. Application Data

[63] Continuation of application No. 08/106,115, Aug. 13, 1993, abandoned.

[51] Int. Cl.$^6$ ........................................................ A61B 5/05
[52] U.S. Cl. ........................... 600/407; 600/411; 600/427
[58] Field of Search ............................ 128/653.1, 653.2, 128/920, 922; 364/413.13, 413.14, 413.16, 413.19; 382/128; 600/407, 410, 425, 427, 417, 411

[56] References Cited

U.S. PATENT DOCUMENTS

| | | | |
|---|---|---|---|
| 4,845,626 | 7/1989 | Ohhashi | 304/413.16 |
| 4,979,222 | 12/1990 | Weber | 382/6 |
| 5,081,992 | 1/1992 | Levin et al. | 128/653.2 |
| 5,099,846 | 3/1992 | Hardy | 364/413.13 X |
| 5,173,946 | 12/1992 | Rao | 382/22 |
| 5,269,305 | 12/1993 | Corol | 128/653.1 |
| 5,285,787 | 2/1994 | Machida | 128/653.2 |
| 5,291,889 | 3/1994 | Kenet et al. | 128/653.1 |

OTHER PUBLICATIONS

Jiang et al., New Approach to 3–D registration of multimodality medical images by surface matching, SPIE Conference: Visualization in Biomedical Computing, Conference No. 17839, Oct. 13–16, 1992.

Liu et al., Partial shape classification using contour matching in distance transformation, IEEE transactions on Pattern Analysis and Machine Intelligence, v12 n11, Nov. 1990, pp. 1072–1079.

Borgefors, Gunilla, Hierarchical chamfer matching: a parametric edge matching: algorithm, IEEE transactions on Pattern Analysis and Machine Intelligence, v10 n6, Nov. 1988, pp. 849–865.

Jiang et al., New approach to 3–D registration of multimodality medical images by surface matching, Proceedings of SPIE—The Inter. Society for Optical Eng., v 1808, conference No. 17839, pp. 196–213, Oct. 13, 1992.

*Primary Examiner*—Brian L. Casler
*Attorney, Agent, or Firm*—Darby & Darby, P.C.

[57] ABSTRACT

This invention relates to the fusion of one data set acquired by either two-dimensional or three-dimensional imaging data acquisition means, such as MRI, onto another data set taken by another imaging means which has been mapped into stereotactic coordinates. As an example, an MRI data set which has intrinsic distortion in its dimensions or linearity can be fused with a CT data set which does not have image distortion, the CT data set being rendered in stereotactic coordinates by a stereotactic localizer means that has been attached to the patient's body. In this way, a distorted data set or a non-stereotactic data set such as the MRI image data can be mapped into a non-distorted or stereotactic data set so as to render the MRI data set in stereotactic coordinates and/or to render it with less distortions in its dimensions.

8 Claims, 1 Drawing Sheet

FUSION OF ANATOMICAL DATA SETS INTO STEREOTACTIC COORDINATES

This application is a continuation of copending application Ser. No. 08/106,115 filed on Aug. 13, 1993 now abandoned.

BACKGROUND TO THE INVENTION

To this date, there have been examples of fusion of one image data set onto another image data set so as to register anatomical images seen in both data sets. One example of this is the work of Pellizari and Chen. They were able to take, for example, an MRI image data set of the brain and a similar CT image data set and surface render the surface of the brain in each of the data sets. They then used a computer algorithm to "stretch" one data set of the brain surface onto the other data set of the brain surface to produce the best registration. This is done using a reduction of the surface to discrete points and minimizing a distance function of the two data sets so as to best fit one to the other. Although the two data sets may be taken from two-dimensional tomographic slices and then stacked into a three-dimensional data set volume, the surfaces of the anatomy or other structures may be segmented or separated out into their own sub-set for the purposes of such image fusion.

Another example of prior art is the work of one of the authors, Marcelle Herk, in registration of two-dimensional images seen from a portal imager on a linear accelerator (LINAC), and comparing that to other two-dimensional images taken from previous X-rays. The technique which was used is the so-called "Chamfer technique," which relates to a distance transform and a minimization principle to map two similar anatomical structures or features onto each other. Separation of a sub-set of anatomical data can be done by a process called segmentation, which separates out the sub-structures and related data points based on, for example, intensity or other image parameters. This would enable, for example, the skull, the ventricles, or the cortex of the brain to be segmented in an MRI or a CT image.

There is, however, an outstanding problem in medical imaging which heretofore was not resolved. That is to take a data set such as MRI imaging, which is rendered in a three-dimensional volume based on a series of two-dimensional slices or a three-dimensional data collection set, and relate it to a stereotactically derived CT image data set of the same anatomy. The problem with the MRI data set is that it typically has intrinsic distortions. The problem with a CT data set is that although each individual two-dimensional slice of a stack of two-dimensional images may have a good metric or distance dimension from the CT scan, it is often unknown where the slice is in relation to external apparatus or body-fixed apparatus. By doing a proper transformation of the CT data set into a stereotactic space related to an external apparatus, these problems can be overcome.

It is thus an object of the present invention to provide a means whereby, in combination, two large image data sets, such as for an MRI image data set and a CT data set, can be fused together by a computer algorithm, and one of the data sets can be put into a faithful stereotactic frame of reference so that all of the points in three dimensions have an accurate spatial representation relative to each other. Thereafter, the second data set, which may have intrinsic distortion, can be fused with the first data set, which is rendered in a known stereotactic coordinate system, thereby providing an accurate dimension scale and stereotactic coordinate set for the second distorted data set. An example of this is to take a distorted MRI image data set with no stereotactic reference markers and fuse it with a CT data set, which has been acquired, with a stereotactic localizer in place on the patient's body, thereby providing an accurate rendering of the MRI data in stereotactic coordinates.

DESCRIPTION OF THE INVENTION

Figure 1:
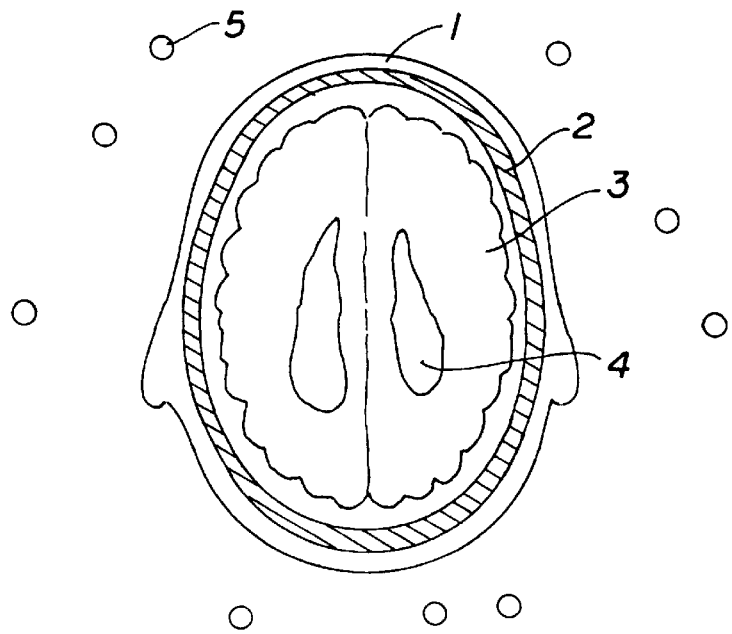
FIG. 1 shows a schematic drawing of a two-dimensional CT scan through the anatomy of the head with stereotactic fiducial markers present.

Referring to FIG. 1, there is illustrated a schematic two-dimensional CT tomographic slice using X-rays through a patient's head. There is the scalp or skin 1, the skull 2, and the brain parenchyma with its cortex 3, and the ventricle 4 seen in the slice. Other structures will also be visible. In addition, there are index markers, illustrated by the spot 5, which correspond to the intersection of the CT slice with a localizer structure that is secured relative to the patient's head, typically via a head ring. This is common technology and is illustrated by the BRW and CRW Stereotactic Systems of Radionics, Inc., Burlington, Mass. The multiplicity of index markers 5 enables an exact mathematical calculation of the relative position and angulation of the two-dimensional CT slice through the patient's head relative to a stereotactic coordinate system. The stereotactic coordinate system is typically referenced to a head ring or base frame which is attached to the patient's anatomy, typically by means of head posts and head screws which are anchored to the patient's skull. Thus, the stereotactic coordinate system is usually referenced to external apparatus, and the two-dimensional CT data space can be transformed or mapped, pixel by pixel, into the coordinate system referred to as the stereotactic coordinate system. In this way, the CT data for every CT slice can be put into "stereotactic space." It is a characteristic of the X-ray CT scan that the linearity and dimensional determinations in each scan are very accurate. This means that distances can be determined between points in the anatomy seen in FIG. 1 with relatively high accuracy. This accuracy can typically be well under 1 mm. It is therefore true that the two-dimensional data, when transformed into stereotactic coordinate space, also retains this dimensional accuracy, or metric accuracy. It is common at this time to take stacks of such two-dimensional tomographic slices and store them into a graphics computer workstation and render them in three dimensions as a three-dimensional volume representation. It is also typical to "segment" anatomical structures, such as the scalp 1, the skull 2, the brain 3, or the ventricle 4, or even a pathological structure such as a tumor, cyst, or arterovenous malformation, and separate out such distinct anatomical structures into 3-D volume renderings in the computer workstation. It is thus possible to plan surgery three-dimensionally prior to opening the patient's head and visualize most of the critical and pathological structures relative to the external or brain anatomy.

Figure 2:
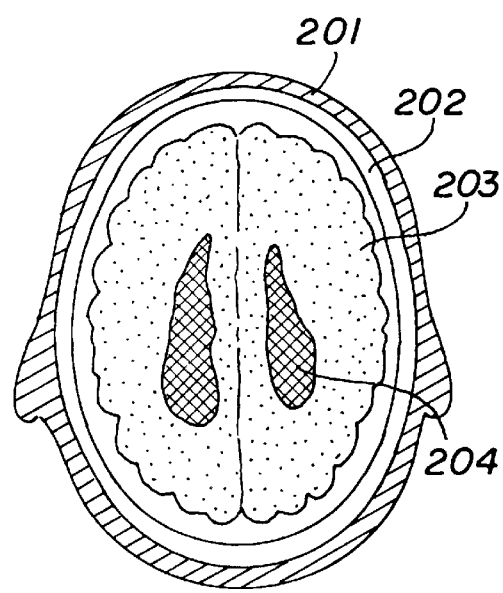
FIG. 2 shows a schematic diagram of a two-dimensional MRI slice through the cranial anatomy, as in FIG. 1.

FIG. 2 illustrates a typical two-dimensional slice from an MRI magnetic resonance imaging scanner. One also can visualize structures such as the scalp 201, the skull 202, and the brain 203, and the ventricles 204. However, these structures typically render themselves with different contrasts and "gray scales" and, in some cases, either more visible or less visible relative to the CT scan illustrated in FIG. 1. Other types of scanning modalities, such as P.E.T. proton emission tomography, ultrasound, and other methods, are being developed and could equally be used as illustrations in FIG. 1 and FIG. 2.

Considering FIG. 2 is an MRI scan, which can be taken in either two-dimensional slices or on a full three-dimensional volume acquisition, the distance or linear metric accuracy of such a scan has characteristic distortions which are difficult to trace. Furthermore, the scale and the slice orientation of FIG. 2 may be totally different from that of FIG. 1. It is an outstanding problem in radiographic imaging to be able to "fuse" such two images and superimpose them one upon the other. The reason is that enhanced anatomy seen in one is often required to be known relative to anatomy that is only visible in the other. Furthermore, because MRI scan has intrinsic distortion, it is very important to be able to fuse it onto something which has no distortion, such as a CT scan, so as to get accurate spatial information from the very valuable MRI imaging. It is a further need in stereotactic applications, where pinpoint precision of placement of probes or beams into the brain is required, that such MRI data be put into "stereotactic" space or a stereotactic coordinate system for precision surgery or diagnosis.

The present invention relates to the method and calculation of fusing such an amorphous or distorted image space into a non-distorted and stereotactically registered image space. This has been carried out by the inventors on a computer graphic workstation for image distorted images fused with stereotactic CT images. To be specific about how this is done, the segmented images of a given anatomical structure, such as the scalp 1 in FIG. 1 and the scalp 201 in FIG. 2, is segmented in each of the two-dimensional or three-dimensional data sets. Then a randomly generated sub-set of data points is sampled from these two segmented anatomical image spaces. The "Chamfer" technique is now used to best fit these two sub-sets of points, one relative to the other. This is done by a minimization principle in which one set of data points is translated, rotated, and stretched in several axis directions so as to reduce a distance function between respective points. Such a computation can be done relatively rapidly in modern-day computer workstations. There are several methodologies for achieving such best fits between two sets of collections of three-dimensional data points. The fusing algorithm in which various degrees of freedom are varied for one data set to match it in a best-fit fashion to the other data set, also varied, can take on several mathematical forms.

This method can be done for three-dimensional volume data sets or for two-dimensional data sets. A three-dimensional data set would be acquired by a stack of two-dimensional data sets, as in the CT tomographic situation. No slice-to-slice knowledge between the two data sets is required to produce the fusion described above. That is to say, if one has two distinct three-dimensional data sets, each having been acquired by a stack of two-dimensional data sets involving tomographic slices, then no predetermined registration of the tomographic data slices in the two data sets is required to produce the fusion of the three-dimensional data set.

By the above method, therefore, one set of data, which may be registered in stereotactic coordinates by the method described in connection with FIG. 1, may be mapped onto and fused with a second data set, as illustrated by the tomographic slice in FIG. 2 which is not in stereotactic coordinate space. Thereby, that second data set, which may have substantial distortion and not be predetermined in stereotactic coordinates, can be described in stereotactic coordinates and be undistorted by this method of fusion. These are among two of the important and novel objectives of this invention.

Another objective of the present invention which follows from the above description is that once the second data set, which is not in stereotactic coordinates, has been fused in a three-dimensional way, as described above, then two-dimensional reconstructions from that three-dimensional data set can be done after the fusion so that the slices correspond to the two-dimensional slices used in the acquisition of the first data set. In this way, therefore, the fusion process provides a way of producing exactly corresponding two-dimensional data set from an otherwise non-corresponding, initial set of two-dimensional data sets. This can be very useful for comparative radiology in which, for example, it is desirable to compare an MRI two-dimensional image with a CT two-dimensional image and to have those two-dimensional images correspond to the same slice to the patient anatomy. Doing a CT scan or an MR scan without such a fusion technique described here would make it relatively difficult to do identical slicing in the MR and the CT scanning phase. Whereas after the fusion process, such exactly corresponding slices can be derived from the reconstructed images of the three-dimensional volume data.

It is noted that new CT scanners can take tomographic data in a three-dimensional fashion very quickly. One example of this is the Siemens spiral tomographic scanner, which takes a rapid series of CT X-ray beam data, essentially in one session. Included in the scope of this patent is the acquisition of such quasi-three-dimensional data for the CT scanner.

It is noted that the illustrations used to describe this invention are taken from the cranial anatomy, however, this could be extended easily to examples in the rest of the body.

Examples of this invention are shown for two-dimensional data, as in FIGS. 1 and 2. However, it is equally well suitable for examples of full three-dimensional data sets where segmentation of anatomy are done directly from three-dimensional data sets themselves.

Figure 3:
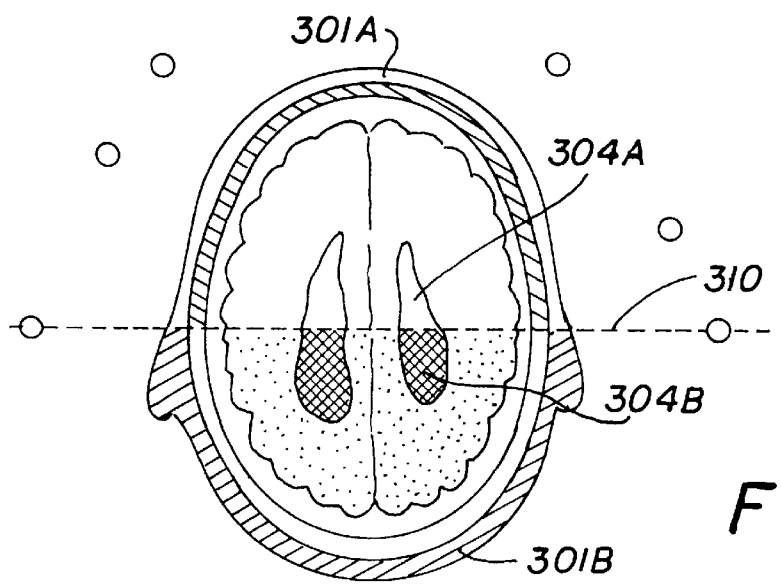
FIG. 3 shows a method of comparing two tomographic image slice data sets on the same screen with a scroll capability for detailed metric comparison.

Another aspect of the present invention is illustrated in FIG. 3. The dashed line 310 represents a scroll line, above which is shown, for example, the image datas from a first set of scanning, such as in FIG. 1, and below the line is a set of image data from the second set of imaging data, as in FIG. 2. Thus, an added aspect of the present invention is the corresponding representation of these two image data sets before and/or after fusion to illustrate their correspondence, or lack thereof, one relative to the other. This representation of the two data sets on the same screen can be done by using different colors for the two different data sets, superposition of the data one on top of the other, or by division of the screen, as with line 310, so that one data set is shown above it, and the other data set is shown below it. The line 310 can be scrolled back and forth over the data set (from top to bottom and back) in FIG. 3 so as to see the details of the matching or fusion at the position of the line 310. Structures 301A and 304A correspond to analogous structures in FIG. 1 of the first tomographic data sets, and the structures 304B and 301B correspond to analogous structures for the second data set, as may be indicated in FIG. 2. By scrolling line 310 up and down over the figure, one can observe the details of these analogous structures as they pass one another at the boundary interface of the scroll line 310. In this way, exquisite detail and comparison of two tomographic data sets, either in a two-dimensional representation or in a reconstructed two-dimensional or three-dimensional representation, can be done.

To those skilled in the art, there are many ways of achieving the fusion of two-dimensional or three-dimensional geometric patterns or data sets. Although we have described here and referred to the Chamfer method, there may be others available in mathematical computer science and analytic methods. The examples above are not intended to limit the invention to CT or MRI imaging, but could be applied to a large variety of other imaging techniques such as ultrasound, P.E.T., SPECT, or other imaging modalities of the future. Each data set may be taken from the same imaging modality, as for example fusing CT with CT or fusing MRI with MRI data.

Having described the invention by the above illustrations, what we claim by U.S. Letters Patent are the following:

1. A method for image fusion of anatomical image data of a patient's body including:

a. taking a first tomographic data set of said patient's body using a first tomographic scanner, said first tomographic data set being taken with a graphic localizer positioned near said patient's body so that said first tomographic data set is registered into a stereotactic coordinate system determined by a plurality of images of said graphic localizer in said first tomographic data set;

b. taking a second tomographic data set of said patient's body;

c. storing said first and second tomographic data sets in a computer;

d. fusing mathematically by a fusion program in said computer said first tomographic data set onto said second tomographic data set by fitting similar anatomical structures in said two tomographic data sets;

e. and transforming said second tomographic data set into registration with said first tomographic data set, and thus into registration with said stereotactic coordinate system.

2. The method of claim 1 wherein:

a. said first tomographic data set is accurate in its linear dimensions;

b. said second tomographic data set has distortions in its dimensions;

c. said method, further including the step of comparing said transformed second tomographic data set with said first tomographic data set after said mathematical fusion step on a graphics display in connection with said computer so as to visually check the quality of said image fusion; and checking and reducing said distortion in said second tomographic data set.

3. The method of claim 2 wherein:

said comparing step includes taking similar two-dimensional slice image data from said first tomographic data set and said transformed second tomographic data set and superimposing said two-dimensional slice image data on said graphics display.

4. The method of claim 1 wherein said first and second tomographic data sets are composed of stacks of two-dimensional slice image data, and including the step of:

a. transforming said two-dimensional slice image data into three-dimensional image data sets for both said tomographic data sets, and wherein:

b. said fusing step includes mathematically fusing similar anatomical structures identifiable in both said three-dimensional image data sets.

5. A method of image fusion of image data of a patient's body taken by tomographic scanner, comprising the steps of:

a) taking a first tomographic image data set of said patient's body with respect to a stereotactic coordinate system using a first tomographic scanner;

b) taking a second tomographic image data set of said patient's body using a second tomographic scanner; and, c) fusing said first tomographic image data set with said second tomographic image data set, wherein said step of fusing said first tomographic image data set with said second tomographic image data set further comprises transforming said second tomographic image data set into registration with said first tomographic image data set and said stereotactic coordinate system.

6. A method of image fusion of image data of a patient's body taken by tomographic scanner, comprising the steps of:

a) taking a first tomographic image data set of said patient's body with respect to a stereotactic coordinate system using a first tomographic scanner;

b) taking a second tomographic image data set of said patient's body using a second tomographic scanner;

c) storing said first tomographic image data set and said second tomographic data set in a computer; and, d) fusing by fusion software in said computer said first tomographic image data set with said second tomographic image data set, wherein said step of fusing by said fusion software in said computer said first tomographic image data set with said second tomographic image data set further comprises transforming said second tomographic image data set into registration with said first tomographic image data set and said stereotactic coordinate system.

7. A system for image fusion of image data of a patient's body taken by tomographic scanner, comprising:

a) a first tomographic scanner for obtaining a first tomographic image data set of said patient's body taken with respect to a stereotactic coordinate system;

b) a second tomographic scanner for obtaining a second tomographic image data set of said patient's body; and c) a computer adapted to accept said first tomographic image data set and said second tomographic image data set and containing fusion software that fuses mathematically said first tomographic image data set with said second tomographic image data set, wherein said fusion software transforms said second tomographic image data set into registration with said first tomographic image data set and said stereotactic coordinate system.

8. A system for image data fusion of image data taken of a patient's body by image scanners, comprising:

a) a localizer structure that is referenced to a stereotactic coordinate system and that is adapted to be placed near the patient's body during tomographic image scanning;

b) a first tomographic scanner for obtaining a first tomographic image data set of said patient's body, said first tomographic image data set containing index mark data corresponding to an image of said localizer structure placed near said patient's body during scanning using said first tomographic scanner which references said first tomographic image data set with respect to said stereotactic coordinate system;

c) a second tomographic scanner for obtaining a second tomographic image data set of said patient's body; and, d) a computer adapted to accept said first tomographic image data set and said second tomographic image data set and containing fusion software that fuses mathematically said first tomographic image data set with said second tomographic image data set, wherein said fusion software transforms said second tomographic image data set into registration with said first tomographic image data set and therefore referenced with respect to said stereotactic coordinate system.

* * * * *